(12) United States Patent
Chazalet et al.

(10) Patent No.: US 6,762,173 B2
(45) Date of Patent: Jul. 13, 2004

(54) FUNGICIDAL COMPOSITION COMPRISING A 2-IMIDAZOLIN-5-ONE

(75) Inventors: Maurice Chazalet, Anse (FR); Marie-Pascale Latorse, Sourcieux Les Mines (FR); Richard Mercer, Ecully (FR)

(73) Assignee: Bayer CropScience SA, Lyons (FR)

( * ) Notice: Subject to any disclaimer, the term of this patent is extended or adjusted under 35 U.S.C. 154(b) by 97 days.

(21) Appl. No.: 10/099,076

(22) Filed: Mar. 13, 2002

(65) Prior Publication Data

US 2002/0132841 A1 Sep. 19, 2002

Related U.S. Application Data

(62) Division of application No. 09/077,988, filed on Sep. 14, 1999, now Pat. No. 6,384,067.

(30) Foreign Application Priority Data

Dec. 2, 1997 (WO) ................................ PCT/FR97/02170

(51) Int. Cl.⁷ ........................ A01N 57/00; A01N 43/50; A61K 31/66
(52) U.S. Cl. ........................................ 514/75; 514/398
(58) Field of Search ........................ 424/405; 504/139; 514/398, 75

(56) References Cited

U.S. PATENT DOCUMENTS 5,637,729 A 6/1997 Lacroix et al. .......... 548/316.7

6,002,016 A 12/1999 Lacroix et al. .......... 548/318.1

FOREIGN PATENT DOCUMENTS

| EP | 0 551 048 | 7/1993 |
| FR | 2 751 845 | 2/1998 |
| WO | 96/03044 | 2/1996 |
| WO | 9911125 | * 3/1999 |

OTHER PUBLICATIONS

Tomlin, The Pesticide Manual Incorporating the Agrochemicals Handbook, 10$^{th}$ Ed., pp. 843–845 (1995).

English language Abstract of EP 0 551 048 (Jul. 14, 1993).

English language Abstract of FR 2,751,845 (Feb. 06, 1998).

* cited by examiner

*Primary Examiner*—Alton N. Pryor
(74) *Attorney, Agent, or Firm*—Connolly Bove Lodge and Hutz LLP

(57) ABSTRACT

Fungicidal compositions comprising a compound of formula I

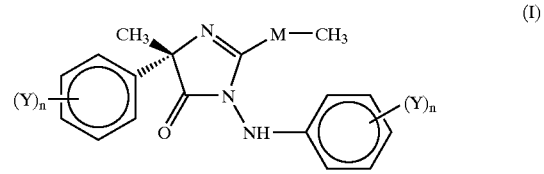

and iprovalicarb and optionally fosetyl-Al.

11 Claims, 9 Drawing Sheets

FIG. 9

Dose of I in mg/liter

Dose of IIG (fencaramide) in mg/liter

IC70 = 34
IC70 = 36
50
50

I/(IIG+IIG') = 1/(1+10)

I/(IIG+IIG') = 2/(1+10)

FUNGICIDAL COMPOSITION COMPRISING A 2-IMIDAZOLIN-5-ONE

CROSS-REFERENCE TO RELATED APPLICATION

The present application is a divisional of, and claims the benefit of, U.S. patent application Ser. No. 09/077,988, which was filed on Sep. 14, 1999 now U.S. Pat. No. 6,384,067, in the names of Maurice Chazalet et al., and was entitled Novel Fungicidal Compositions Comprising a 2-imidazolin-5-one.

The present invention relates to novel fungicidal compositions comprising a 2-imidazolin-5-one, which are intended in particular for protecting crops. The invention also relates to a process for protecting crops against fungal diseases.

Compounds derived from 2-imidazolin-5-ones with fungicidal action are known, in particular from European patent application EP 551,048, these compounds making it possible to prevent the growth and development of phytopathogenic fungi which attack or are liable to attack crops.

International patent application WO 96/03044 also discloses a certain number of fungicidal compositions comprising a 2-imidazolin-5-one in combination with one or more fungicidal active materials.

However, it is always desirable to improve the products which can be used by growers in order to combat fungal diseases of crops, and in particular mildews.

It is also always desirable to reduce the doses of chemical products spread into the environment to combat fungal attacks on crops, in particular by reducing the application doses of the products.

Lastly, it is always desirable to increase the number of antifungal products available to growers in order that they will find, among these products, the one which is best suited to the grower's specific use.

One aim of the invention is thus to provide a novel fungicidal composition which is useful for the problems outlined above.

Another aim of the invention is to propose a novel fungicidal composition which is useful in the preventive and curative treatment of Solanacea diseases.

Another aim of the invention is to propose a novel fungicidal composition which is of improved efficacy against mildew and/or early blight in Solanaceae.

Another aim of the invention is to propose a novel fungicidal composition which is of improved efficacy against mildew and/or oidium and/or botrytis in grapevine.

It has now been found that these aims may be achieved, partly or totally, by means of the fungicidal compositions according to the present invention.

The subject of the present invention is thus, firstly, fungicidal compositions comprising a compound (I) of formula:

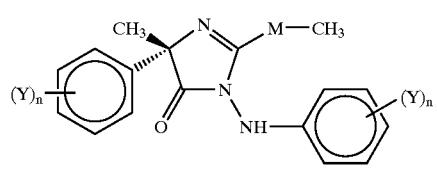

(I)

in which:
M represents an oxygen or sulphur atom;
n is an integer equal to 0 or 1;
Y is a fluorine or chlorine atom or a methyl radical;
and a compound (II) chosen from the group comprising:
  compound (IIA) or propamocarb, also known as propyl 3-(dimethylamino)propyl carbamate;
  a compound (IIB) of formula (IIB)

(IIB)

in which:
  $R_1$ is a nitrogen atom or the —CH group, and
  $R_2$ is a thiomethyl $SCH_3$ group or a diethylamino $N(C_2H_5)_2$ group,
  the compound (IIC) or cyprodinil, also known as 2-phenylamino-4-cyclopropyl-6-methyl-pyrimidine;
  the compound (IID), which is 2-hydroxybenzoic acid or salicylic acid, its esters and its salts, in particular the alkali-metal and alkaline-earth metal salts;
  the compound (IIF) or 8-t-butyl-2-(N-ethyl-N-n-propylamino)methyl-1,4-dioxaspiro[4.5]decane, also known as spiroxamine;
  the compound (IIG) or isopropyl ester of [2-methyl-1-(1-p-tolylethylcarbomyl)propyh] acid, also known as iprovalicarb (sometimes referred to hereinafter by the first proposed name for the compound "fencaramide");
  the compound (IIH) or 4-chloro-2-cyano-1-dimethylsulphamoyl-5-(4-methylphenyl)imidazole;
  the compound (I)/compound (II) ratio being between 0.01 and 50, preferably between 0.1 and 10.

It is clearly understood that the said fungicidal compositions may contain a single compound (II) or more than one such compound, for example 1, 2 or 3 compounds (II) depending on the use for which they are intended.

The composition according to the invention are advantageous for combating, in particular, mildews of the Solanaceae, such as potatoes or tomatoes, as well as for combating mildew and oidium of grapevine.

Compound (I) is known, in particular from patent application EP 629,616.

Compound (IIA), or propamocarb, is a fungicide described in the Pesticide Manual 10th Edition, published by the British Crop Protection Council page 843.

Compound (IIB) and its use are known in particular from European patent applications EP 313,512, EP 420,803 and EP 690,061.

Compound (IIC), or cyprodinil, is described in European patent application EP 310,550.

Compound (IIF) and its use as a fungicide are described in European patent application EP 0,281,842.

Compound (IIG) and its use as a fungicide are described in at least one of the European patent applications EP 0,398,072 or EP 0,472,996.

Compound (IIH) and its use as a fungicide are described in at least one of the European patent applications EP 0,298,196 or EP 0,705,823.

The compound (I)/compound (II) ratio is defined as being the ratio of the weight of these 2 compounds. This is likewise the case for any ratio of 2 chemical compounds, mentioned below in the present text, insofar as a definition different from this ratio is not expressly indicated.

These compositions generally appreciably improve the respective and isolated action of compound (I) and of compound (II) for a certain number of fungi that are particularly harmful in crops, in particular for Solanaceae, more particularly for mildew of Solanaceae while at the same time retaining an absence of phytotoxicity towards these crops. This therefore results in an improvement in the spectrum of activity and the possibility of decreasing the respective dose of each active material used, the latter quality being particularly advantageous for readily appreciated ecological reasons.

BRIEF DESCRIPTION OF DRAWINGS

FIG. 9 shows the efficacy results obtained in Example 12 using ternary mixtures containing different ratios of compound (I) to compounds (IIG) (fencaramide) and (IIG') (Fosetyl-Al).

Figure 1:
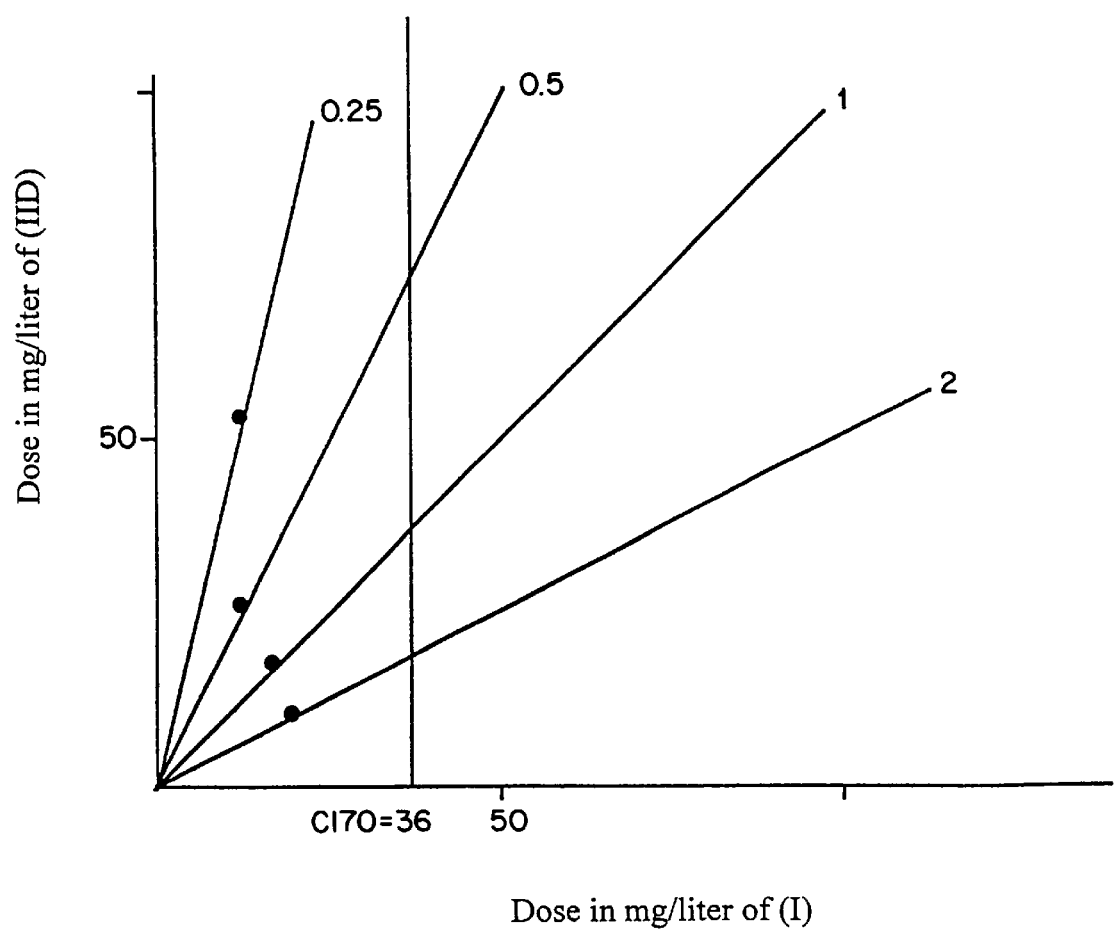
FIG. 1 shows the efficacy results obtained in Example 4 using various ratios of compound (I) and (IID).

The fungicidal compositions according to the invention for which the compound (I) is the compound of formula (I) in which M is a sulphur atom and n is equal to 0, also known as (4S)-4-methyl-2-methylthio-4-phenyl-1-phenylamino-2-imidazolin-5-one, are preferred.

In the compositions according to the invention, the compound (I)/compound (II) ratio is advantageously chosen so as to produce a synergistic effect. The term synergistic effect is understood to refer in particular to that defined by Colby S. R. in an article entitled "Calculation of the synergistic and antagonistic responses of herbicide combinations" published in the journal Weeds, 1967, 15, p. 20–22. The said article uses the formula:

$$E = X + Y - XY/100$$

in which E represents the expected percentage of inhibition of the disease for the combination of the two fungicides at defined doses (for example equal to x and y respectively), X is the percentage of inhibition observed for the disease by the compound (I) at a defined dose (equal to x), Y is the percentage of inhibition observed for the disease by the compound (II) at a defined dose (equal to y). When the percentage of inhibition observed for the combination is greater than E, there is a synergistic effect.

The term synergistic effect is also understood to refer to that defined by application of the Tammes method, "Isoboles, a graphic representation of synergism in pesticides" Netherlands Journal of Plant Pathology, 70 (1964), p. 73–80.

The ranges of the compound (I)/compound (II) ratio indicated above do not in any way limit the scope of the invention, but are rather mentioned as a guide, a person skilled in the art being entirely capable of carrying out complementary tests in order to find other values of the ratio of doses of these 2 compounds for which a synergistic effect is observed.

According to a first preferred variant of the compositions according to the invention, the compound (II) is chosen from the group comprising compounds (IIA), (IIB), (IIC) and (IID). These compositions in particular have advantageous synergistic properties.

According to a more preferred aspect of this first variant of the compositions according to the invention, the compound (II) is compound (IIA) or propamocarb. In this case, particularly improved protection against mildew of Solanaceae is obtained.

In a preferred manner, when the compound (II) is propamocarb, the compound (I)/compound (II) ratio is between 0.01 and 10, preferably between 0.05 and 1 and even more preferably between 0.1 and 1.

According to another more preferred aspect of this first variant of the compositions according to the invention, the compound (II) is compound (IIB).

In this case, the compound of formula (IIB) in which $R_1$ represents —CH and $R_2$ represents —SCH$_3$ is more particularly preferred. The latter compound is the S-methyl ester of 1,2,3-benzothiadiazole-7-carbothioic acid (also known as CGA 245704).

According to another aspect of the first variant of the compositions according to the invention, the compound (II) is compound (IID).

In a preferred manner, when the compound (II) is compound (IIB) or (IID), the compound (I)/compound (II) ratio is between 0.05 and 50, preferably between 0.1 and 10 and even more preferably between 0.1 and 5.

According to another aspect of the first variant of the compositions according to the invention, the compound (II) is compound (IIC).

In a preferred manner, when the compound (II) is compound (IIC), the compound (I)/compound (II) ratio is between 0.05 and 50, preferably between 0.1 and 10 and even more preferably between 0.2 and 1.

According to a third variant of the compositions according to the invention, the compound (II) is compound (IIF).

When the compound (II) is compound (IIF), the compound (I)/compound (II) ratio is preferably between 0.05 and 10, preferably between 0.1 and 5.

According to a fourth variant of the compositions according to the invention, the compound (II) is compound (IIG).

When the compound (II) is compound (IIG), the compound (I)/compound (II) ratio is preferably between 0.25 and 5, preferably between 0.5 and 4.

According to an even more preferred embodiment of the compositions according to the invention, they advantageously comprise, in the latter case, besides the compounds (I) and (IIG), a compound (IIG') chosen from:
 the salts of a monoalkyl phosphite and of a mono-, di- or trivalent metal cation, such as fosetyl-Al, or
 phosphorous acid and its alkali-metal or alkaline-earth metal salts.

The (IIG)/(IIG') molar ratio of the compounds (IIG) and (IIG') is generally between 0.037 and 0.37, preferably between 0.018 and 1.8. For the purposes of the present invention, the expression (IIG)/(IIG') molar ratio is understood to refer to the ratio calculated in the following way. The numerator of this ratio is equal to the number of moles of the compound (IIG). The denominator of this ratio is equal to the number of moles of the compound (IIG') multiplied by the number of moles of phosphorous acid resulting from the hydrolysis of one mole of compound (IIG'). Phosphorous acid is the compound of empirical formula $H_3PO_3$.

Fosetyl-Al is preferably used as compound (IIG'). The (IIG)/(IIG') weight ratio of the compounds (IIG) and (IIG') is, in this case, between 0.01 and 1, preferably between 0.05 and 5.

According to a fifth variant of the compositions according to the invention, the compound (II) is compound (IIH). In this case, the compound (I)/compound (II) ratio is between 0.05 and 5, preferably between 0.5 and 2.

Besides the compound (I) and the compound (II), the compositions according to the invention comprise an agriculturally suitable inert support and optionally an agriculturally suitable surfactant. In the following text, the term active material denotes the combination of the compound (I) with the compound (II), and the percentages quoted are, except where otherwise mentioned, weight/weight percentages.

In the present description, the term "support" denotes an organic or inorganic, natural or synthetic material with which the active material is combined in order to facilitate its application onto the plant or onto the soil. This support is thus generally inert and should be agriculturally acceptable, in particular on the crop treated. The support may be solid (in particular: clays, natural or synthetic silicates, silica, resins, waxes, solid fertilizers) or liquid (in particular: water, alcohols, ketones, petroleum fractions, aromatic or paraffinic hydrocarbons, chlorohydrocarbons, liquefied gases).

The surfactant may be an emulsifying, dispersing or wetting agent of ionic or nonionic type. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyltaurates) and phosphoric esters of polyoxyethylated phenols or alcohols. The presence of at least one surfactant is often required since the active material and/or the inert support are not water-soluble and the vector agent for the application is water.

These compositions may also contain other ingredients of any kind such as, for example, protective colloids, adhesives, thickeners, thixotropic agents, penetration agents, stabilizers, sequestering agents, pigments, dyes or polymers.

More generally, the compositions according to the invention may be combined with any solid or liquid additives corresponding to the usual techniques of agrochemical formulation.

The application techniques are well known to those skilled in the art and they may be used without inconvenience in the context of the present invention. Mention may be made, for example, of spraying.

Among the compositions, solid or liquid compositions may be mentioned generally.

As forms of solid compositions, mention may be made of powders for dusting or dispersion (with an active material content which may be up to 100%) and granules, in particular those obtained by extrusion, by compacting, by impregnation of a granular support or by granulation of a powder (the active material content in these granules being between 1 and 80% for the latter cases).

The compositions may also be used in the form of a powder for dusting; a composition comprising 50 g of active material, 10 g of finely divided silica, 10 g of organic pigment and 970 g of talc may thus be used; these constituents are mixed together and ground and the mixture is applied by dusting.

As liquid composition forms or forms intended to constitute liquid compositions during application, mention may be made of solutions, in particular water-soluble concentrates, emulsifiable concentrates, emulsions, concentrated suspensions, aerosols, wettable powders (or powder to be sprayed), pastes and dispersible granules.

The emulsifiable or soluble concentrates usually comprise 10 to 80% of active material, the ready-to-apply emulsions or solutions themselves containing 0.01 to 20% of active material.

For example, in addition to the solvent, the emulsifiable concentrates may contain, whenever necessary, 2 to 20% of suitable additives such as the stabilizers, surfactants, penetration agents, corrosion inhibitors, dyes or adhesives mentioned above.

Starting with these concentrates, emulsions of any desired concentration may be obtained by dilution with water.

The concentrated suspensions, which may also be applied by spraying, are prepared so as to obtain a stable fluid product which does not separate on settling and they usually contain from 10 to 75% of active material, from 0.5 to 15% of surfactants, from 0.1 to 10% of thixotropic agents, from 0 to 10% of suitable additives, such as pigments, dyes, antifoaming agents, corrosion inhibitors, stabilizers, penetration agents and adhesives and, as support, water or an organic liquid in which the active material is sparingly soluble or insoluble: certain solid organic materials or inorganic salts may be dissolved in the support in order to help prevent sedimentation, or as antifreezes for the water.

The wettable powders (or powder to be sprayed) are usually prepared such that they contain 20 to 95% of active material, and they usually contain, in addition to the solid support, from 0 to 5% of a wetting agent, from 3 to 10% of a dispersing agent and, whenever necessary, from 0 to 10% of one or more stabilizers and/or other additives, such as pigments, dyes, penetration agents, adhesives, anticaking agents, etc.

In order to obtain these powders to be sprayed or wettable powders, the active materials are mixed intimately in suitable mixers with additional substances and are ground using mills or other suitable grinders. Powders to be sprayed whose wettability and placing in suspension are advantageous are thus obtained; they may be placed in suspension with water at any desired concentration.

In place of wettable powders, pastes may be prepared. The conditions and modes of preparation and of use of these pastes are similar to those for the wettable powders or powders to be sprayed.

The dispersible granules are usually prepared by agglomeration, in suitable granulation systems, of the compositions of wettable powder type.

As has already been stated, the aqueous emulsions and dispersions, for example the compositions obtained by diluting a wettable powder or an emulsifiable concentrate according to the invention with water, are included within the general scope of the present invention. The emulsions may be of the water-in-oil or oil-in-water type and they may have a thick consistency such as that of a "mayonnaise".

The fungicidal compositions according to the invention usually contain from 0.5 to 95% of the combination of compound (I) and compound (II).

This may be the concentrated composition, that is to say the commercial product combining compound (I) and compound (II). It may also be the dilute composition ready to be applied to the crops to be treated. In the latter case, the dilution with water may be carried out either using a commercial concentrated composition containing compound (I) and compound (II) (this mixture is referred to as the "ready-to-use" mixture or "ready mix"), or using a mixture prepared at the time of use (known as the "tank mix") of two commercial concentrated compositions each containing compound (I) and compound (II).

Lastly, the subject of the invention is a process for curatively or preventively combating the phytopathogenic fungi of crops, characterized in that an effective and non-phytotoxic amount of a fungicidal composition according to the invention is applied to the vegetation to be treated.

The phytopathogenic fungi of the crops which may be combated by this process are, in particular, those:
of the group of oomycetes:
of the genus Phytophthora such as *Phytophthora infestans* (mildew of Solanaceae, in particular late blight of potato or tomato mildew),
of the family of Peronosporaceae, in particular *Plasmopara viticola* (downy mildew of grapevine), *Plasmopara halstedei* (sunflower mildew), Pseudoperonospora sp (in particular cucurbit mildew and downy mildew of hop), *Bremia lactucae* (mildew of lettuce), *Peronospora tabacinae* (downy mildew of tobacco) and *Peronospora parasitica* (downy mildew of cabbage),
of the group of adelomycetes:
of the genus Alternaria, for example *Alternaria solani* (early blight of Solanaceae and in particular of tomato and potato),
of the genus Guignardia, in particular *Guignardia bidwelli* (black rot of grapevine),
of the genus Oidium, for example powdery mildew of grapevine (*Uncinula necator*); powdery mildew of leguminous crops, for example *Erysiphe polygoni* (powdery mildew of Cruciferae); *Leveillula taurica, Erysiphe cichoracearum, Sphaerotheca fuligena;* (powdery mildew of cucurbits, of composites and of tomato); *Erysiphe communis* (powdery mildew of beetroot and cabbage); *Erysiphe pisi* (powdery mildew of pea and alfalfa); *Erysiphe polyphaga* (powdery mildew of bean and cucumber mildew); *Erysiphe umbelliferarum* (powdery mildew of umbellifera, in particular of carrot); *Sphaerotheca humuli* (hop mildew).

The expression "are applied to the vegetation to be treated" is understood to mean, for the purposes of the present text, that the fungicidal compositions which form the subject of the invention may be applied by means of various treatment processes such as:
spraying a liquid comprising one of the said compositions onto the aerial parts of the said vegetation,
dusting, incorporation of granules or powders into the soil, watering around the said vegetation and, in the case of trees, injection or sprinkling.

The spraying of a liquid onto the aerial parts of the crops to be treated is the preferred treatment process.

The expression "effective and non-phytotoxic amount" is understood to refer to an amount of composition according to the invention which is sufficient to allow the control or destruction of the fungi present or liable to appear on the crops, this amount entailing no symptoms of phytotoxicity for the said crops. Such an amount is liable to vary within a wide range depending on the fungus to be combated, the type of crop, the climatic conditions and the nature of the compound (II) included in the fungicidal composition according to the invention. This amount may be determined by systematic field trials, which are within the capabilities of those skilled in the art.

Under the usual conditions of agricultural practice, an amount of fungicidal composition according to the invention corresponding to a dose of compound (I) of between 10 and 500 g/ha, preferably between 20 and 300 g/ha, generally gives good results.

When the compound (II) is compound (IIA), the amount of fungicidal composition according to the invention advantageously corresponds to a dose of compound (II) of between 50 and 2500 g/ha, preferably between 200 and 1500 g/ha.

When the compound (II) is compound (IIB), the amount of fungicidal composition according to the invention advantageously corresponds to a dose of compound (II) of between 2 and 100 g/ha, preferably between 5 and 50 g/ha.

When the compound (II) is compound (IIC), the amount of fungicidal composition according to the invention advantageously corresponds to a dose of compound (II) of between 20 and 2000 g/ha, preferably between 100 and 550 g/ha.

When the compound (II) is compound (IID), the amount of fungicidal composition according to the invention advantageously corresponds to a dose of compound (II) of between 20 and 5000 g/ha, preferably between 50 and 1000 g/ha.

When the compound (II) is compound (IIF), the amount of fungicidal composition according to the invention advantageously corresponds to a dose of compound (II) of between 100 and 1000 g/ha, preferably between 300 and 800 g/ha.

When the compound (II) is compound (IIG), the amount of fungicidal composition according to the invention advantageously corresponds to a dose of compound (II) of between 50 and 250 g/ha, preferably between 100 and 200 g/ha.

When the compound (II) is compound (IIH), the amount of fungicidal composition according to the invention advantageously corresponds to a dose of compound (II) of between 100 and 400 g/ha, preferably between 150 and 350 g/ha.

The examples which follow are given purely by way of illustration of the invention, which they do not limit in any way.

In these examples, as well as in the figures to which reference is made, compound (I) is understood to denote (4S)-4-methyl-2-methylthio-4-phenyl-1-phenyl-amino-2-imidazolin-5-one and compound (IIB) is understood to denote the S-methyl ester of 1,2,3-benzothiadiazole-7-carbothioic acid (or CGA 245704). Similarly, compound (IIG') is understood to refer to Fosetyl-Al.

EXAMPLE 1

Field Trial of a Composition Comprising Compounds (I) and (IIA) Against Late Blight of Potato (*Phytophthora infestans*)

A composition is used comprising compound (I) in the form of a concentrated suspension at 500 g/l and a composition comprising compound (IIA) or propamocarb in the form of a soluble concentrate at 724 g/l.

These 2 compositions are mixed so as to obtain a compound (I)/compound (IIA) ratio equal to 0.15 to 0.10.

The mixture is applied, after dilution with water, at a rate of 500 l/ha to potatoes 2 months after planting the tubers. The doses applied are indicated in the table below. This application is repeated 5 times every 6 days.

After the 2nd application, contamination is carried out by spraying the *Phytophthora infestans* spores.

The results are observed 3 days after the 5th application. For this, the contamination C (or degree of attack) expressed by the number of blackish marks (caused by the disease) per plot is evaluated visually (relative to an untreated plot which is also contaminated). The efficacy E is calculated according to the so-called Abbott formula:

$$E(\text{in }\%)=[(C_{untreated\ control}-C_{treated\ plot})/C_{untreated\ control}]\times 100$$

The results are collated in the following table:

| Composition tested | Doses (in g/ha) | (I)/(IIA) ratio | Efficacy (in %) |
|---|---|---|---|
| (I) + (IIA) | 100 + 1000 | 0.1 | 96 |
| (I) + (IIA) | 100 + 666 | 0.15 | 95 |

A neighbouring plot treated with mancozeb at a rate of 1600 g/ha gave rise to an efficacy of 90%.

EXAMPLE 2

Example 1 is repeated on a potato field located in another region. The results are observed 12 days after the 5th treatment. For this, and on account of the intensity of the attack of the disease, the percentage of foliar surface destroyed is evaluated.

The efficacy is calculated according to the same formula as above.

For the 0.10 ratio, an efficacy of 79% is obtained and for the 0.15 ratio an efficacy of 77% is obtained.

A neighbouring plot treated with mancozeb at a rate of 1600 g/ha gave rise to an efficacy of 59%.

EXAMPLE 3

Greenhouse Test of a Composition Comprising Compounds (I) and (IIB) Against Downy Mildew of Grapevine (*Plasmopara viticola*):

A suspension of 60 mg comprising compounds (I) and (IIB) in a liquid mixture consisting of 0.3 ml of a surfactant (oleate of polyoxyethylenated derivative of sorbitan) diluted to 10% in water and 60 ml of water is prepared.

The compound (I)/compound (IIB) ratio in the suspensions prepared is equal to:

0.125; 0.25; 0.5; 2.

Cuttings of grapevine (*Vitis vinifera*), Chardonnay variety, are cultivated in pots. When these plants are 2 months old (8- to 10-leaf stage, 10 to 15 cm in height), they are treated by spraying with the above suspensions.

Plants used as controls are treated with a similar suspension but which contains no active material ("formulation blank").

After drying for 4 days, each plant is contaminated by spraying with an aqueous suspension of *Plasmopara viticola* spores obtained from sporulated leaves contaminated 7 days beforehand. These spores are placed in suspension in a proportion of 100,000 units per cm$^3$.

The contaminated plants are then incubated for two days at about 18° C., in an atmosphere of saturated humidity and then for 5 days at 20–22° C. under 90–100% relative humidity.

The results are observed 7 days after contamination, by comparison with the control plants. The contamination C is measured by visual evaluation of the percentage of contaminated foliar surface (whitish appearance). Using C, the efficacy is calculated with the same formula as in Example 1.

The IC90 is calculated from the efficacy.

The IC90 is defined as being the weight of mixture (defined for a fixed ratio of the compounds (I) and (IIB)) which it is necessary to apply in order to obtain an efficacy of 90%. The IC90 is expressed in the form of the corresponding weight of the compound (I) in the mixture per ml of liquid sprayed onto the plants.

The results are collated in the table below:

| Ratio: compound (I)/compound (IIB) | IC90 (mg/l) |
|---|---|
| 0.125 | 17 |
| 0.25 | 17 |
| 0.5 | 20 |
| 1 | 35 |
| 2 | 18 |

EXAMPLE 4

Greenhouse Test of a Composition Comprising Compound (I) and the Sodium Salt of Salicylic Acid (Compound IID) Against Late Blight of Potato (*Phytophthora infestans*):

A concentrated suspension of compound (I) and an aqueous solution of the sodium salt of salicylic acid are used.

These 2 liquids are mixed together so as to obtain a compound (I)/compound (IID) ratio equal to: 0.25–0.5–1 and 2.

Potato plants (Bintje variety) are cultivated in pots. When these plants are one month old (5- to 6-leaf stage, 12 to 15 cm in height), they are treated by spraying with a liquid comprising one of the compounds (I) and (IID) either alone or as a mixture in the ratio indicated above.

After 4 days, each plant is contaminated by spraying with an aqueous suspension of spores (30,000 sp/cm$^3$) of *Phytophthora infestans*.

After this contamination, the potato plants are incubated for 5 days at about 18° C. in an atmosphere of saturated humidity.

The results are obtained 5 days after placing in incubation, by comparison with untreated control plants which are also contaminated.

The efficacy results obtained are reported in the form of points, corresponding to 70% destruction of the parasite, and placed in a Tammes diagram which includes the doses of compound (I) expressed in mg/l on the x-axis and the doses of compound (IID), also in mg/l, on the y-axis.

The diagram of FIG. 1 is obtained, in which it appears that, when it is applied alone, the sodium salt of salicylic acid has no efficacy under the test conditions. It appears, however, that the addition of this salt makes it possible, entirely unexpectedly, to lower the dose of compound (I) required to destroy 70% of the parasite to below 36 mg/l, which corresponds to the dose of compound (I) alone which needs to be applied in order to obtain this same percentage of destruction.

The arrangement of the points obtained thus indicates a unilateral effect, which is termed according to the Tammes method mentioned above as a "one-sided effect". This arrangement corresponds to a type-II isobole according to the said method (page 74 of the corresponding bibliographic reference already mentioned) and is characteristic of synergism.

EXAMPLE 5

In Vivo Greenhouse Test of the Combination of Compound (I) with Compound (IIA), Propamocarb, on *Plasmopara viticola* (Downy Mildew of Grapevine) by Preventive Treatment at 4 Days:

A soluble concentrate containing 722 g/l of propamocarb and a 70% dispersible granule of compound (I) are used.

Dilute suspensions corresponding to a spraying volume of 500 l of spraying liquid per ha are prepared from these compositions by dilution with water.

These 2 liquids are mixed together so as to obtain a ratio: compound (I)/propamocarb, equal to: 0.015–0.125–0.5.

Cuttings of grapevine (*Vitis vinifera*), Chardonnay variety, are cultivated in pots. When these plants are 2 months old, they are treated by spraying with the above liquids, taken individually or as a mixture.

After 4 days, each plant is contaminated by spraying with an aqueous suspension of spores of *Plasmopara viticola* obtained from sporulated leaves contaminated 7 days beforehand. These spores are placed in suspension in a proportion of 100,000 units per $cm^3$.

The contaminated plants are then incubated for two days at about 18° C. in an atmosphere of saturated humidity and then for 5 days at 20–22° C. under 90–100% relative humidity.

The results are read 7 days after the contamination, by comparison with the control plants, that is to say untreated but contaminated plants.

The surface area of leaves showing a whitish appearance on their underside, corresponding to attack by the fungus, is assessed visually and the degree of attack is obtained by dividing by the total foliar surface.

The efficacy is then calculated using the Abbott formula and using the result on the control plant.

The efficacy results are reported in the form of points, corresponding to an efficacy of 90%, and placed in a Tammes isobole diagram which includes the doses of the compound (I) expressed in mg/l on the x-axis and the doses of propamocarb, also in mg/l, on the y-axis.

Figure 2:
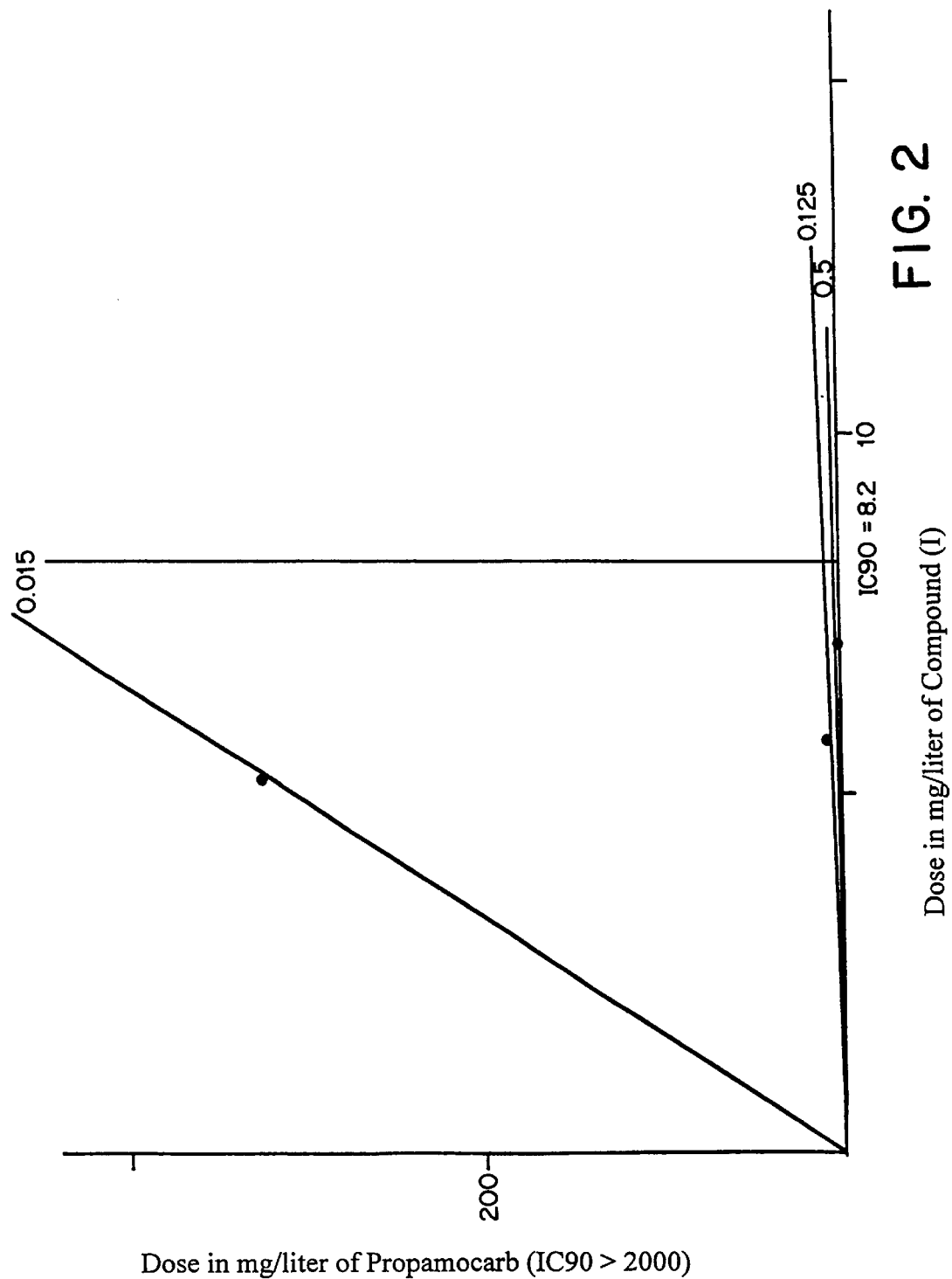
FIG. 2 shows the efficacy results obtained in Example 5 using various ratios of compound (I) and propamocarb.

The diagram of FIG. 2 is obtained, in which it appears that, when it is applied alone, the propamocarb has no efficacy under the test conditions. It appears, however, that the addition of propamocarb makes it possible, entirely unexpectedly, to lower the dose of compound (I) needed to destroy 90% of the parasite to below 8.2 mg/l, which corresponds to the dose of compound (I) alone which needs to be applied to obtain the same efficacy.

The arrangement of the points obtained thus indicates a unilateral effect, termed according to the Tammes method mentioned above as a "one-sided effect". This arrangement corresponds to a type-II isobole according to the said method (page 74 of the corresponding bibliographic reference already mentioned) and is characteristic of synergism.

EXAMPLE 6

In Vivo Greenhouse Test of a Composition Comprising Compounds (I) and (IIA) (Propamocarb) on *Phytophthora infestans* (Late Blight of Potato) by Preventive Treatment at 4 Days:

A soluble concentrate containing 722 g/l of propamocarb and a 70% dispersible granule of compound (I) are used.

Dilute suspensions corresponding to a spraying volume of 1000 l of spraying liquid per ha are prepared from these compositions by dilution with water.

These 2 liquids are mixed together so as to obtain a compound (I)/propamocarb ratio equal to: 0.125–0.25–1.

Potato plants (Bintje variety) are cultivated in pots. When these plants are one and a half months old, they are treated with the above liquids, taken individually or as a mixture.

4 days after the treatment, lamellae are cut off and placed on moistened filter paper in a Petri dish, and these lamellae are contaminated by applying 10 drops of an aqueous suspension of spores (containing 30,000 $sp/cm^3$) of *Phytophthora infestans*.

Next, the potato lamellae are incubated for 3 days at about 18° C. in an atmosphere of saturated humidity.

The results are observed 4 days after the contamination, by comparison with the control plants.

The surface area of the lamellae having a greyish appearance, corresponding to attack by the fungus, is assessed visually and the degree of attack is obtained by dividing this surface area by the total surface of the lamellae.

The efficacy is then calculated using the Abbott formula and using the result on the lamellae used as control.

The results obtained are reported in the form of points, corresponding to 90% destruction of the parasite, and are placed in a Tammes diagram which includes the doses of compound (I) expressed in mg/l on the x-axis and the doses of propamocarb, also in mg/l, on the y-axis.

Figure 3:
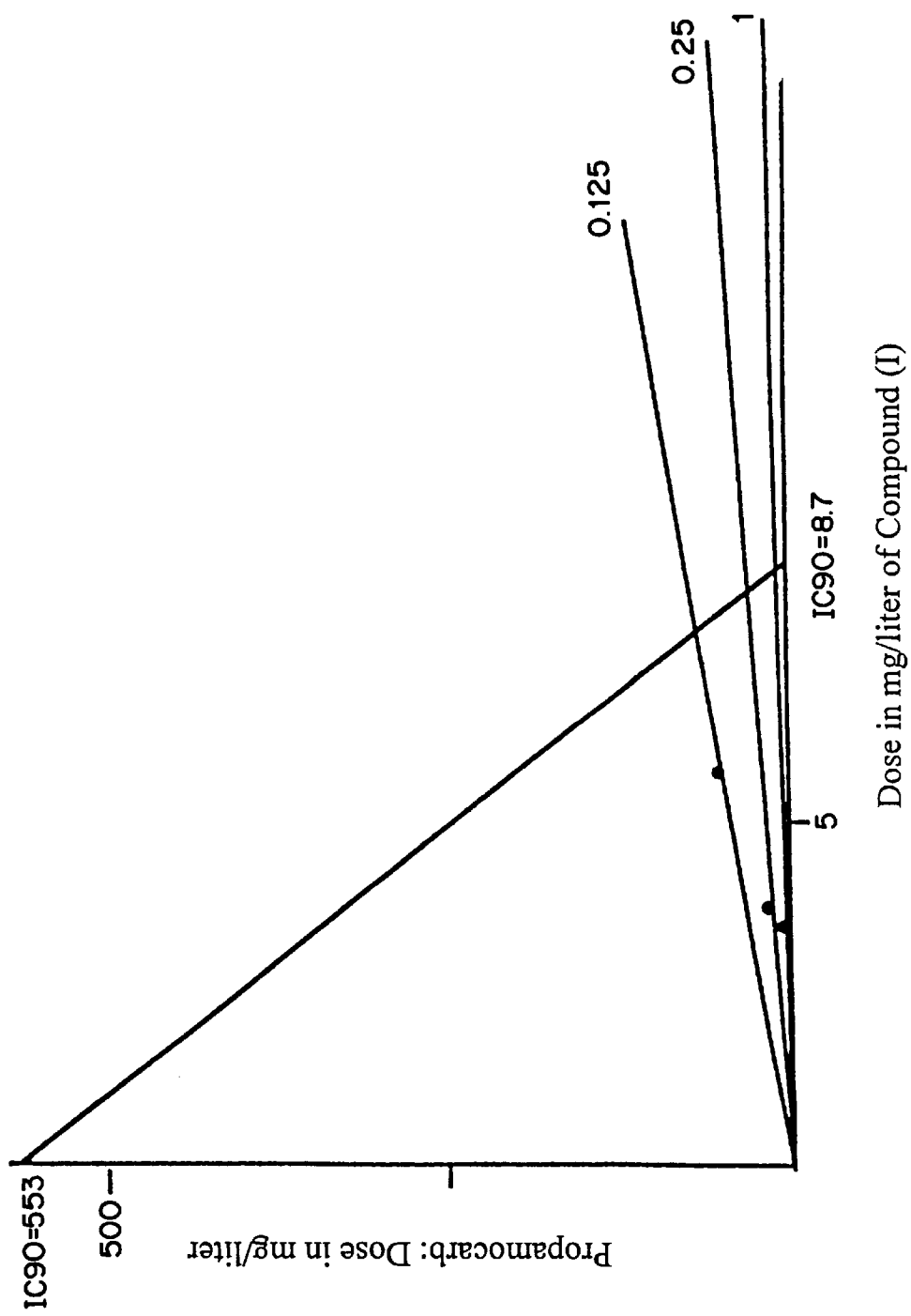
FIG. 3 shows the efficacy results obtained in Example 6 using various ratios of compound (I) and propamocarb.

The diagram of FIG. 3 is obtained, in which it appears that the addition of a dose of compound (I) of less than 8.7 mg/l (which corresponds to the dose of compound (I) alone which needs to be applied in order to obtain 90% destruction of the parasite) makes it possible, entirely unexpectedly, to lower the dose of propamocarb needed to destroy 90% of the parasite to below 553 mg/l (this value corresponding to the dose of propamocarb alone which needs to be applied in order to obtain this same percentage of destruction).

The arrangement of the points obtained thus indicates a bilateral effect, termed according to the Tammes method mentioned above as a "two-sided effect". This arrangement corresponds to a type-III isobole according to the said method (page 75 of the corresponding bibliographic reference already mentioned) and is characteristic of synergism.

EXAMPLE 7

In Vivo Greenhouse Test of a Composition Comprising Compounds (I) and (IIB) (CGA 245704) Against Late Blight of Potato (*Phytophthora infestans*):

A suspension of 60 mg comprising compounds (I) and (IIB) in a liquid mixture consisting of 0.3 ml of a surfactant (oleate of polyoxyethylenated derivative of sorbitan) diluted to 10% in water and 60 ml of water is prepared.

The compound (I)/compound (IIB) ratio in the suspensions prepared is equal to 0.125; 0.25; 0.5; 1.

Potato plants (Bintje variety) are cultivated in pots. When these plants are one and a half months old, they are treated with the above liquids, taken individually or as a mixture.

4 days after the treatment, the plants are contaminated by spraying with an aqueous suspension of spores (containing 30,000 $sp/cm^3$) of *Phytophthora infestans*.

Next, the potato plants are incubated for 5 days at about 18° C. in an atmosphere of saturated humidity.

The results are observed 5 days after the contamination, in comparison with the control plants.

The foliar surface having a greyish appearance, corresponding to attack by the fungus, is assessed visually and the degree of attack is obtained by dividing this surface area by the total surface of the leaves.

The efficacy is then calculated using the Abbott formula and using the result on the control plant.

The results obtained are reported in the form of points, corresponding to 70% efficacy against the parasite, and are placed in a Tammes diagram which includes the doses of compound (I) expressed in mg/l on the x-axis and the doses of CGA 245704, also in mg/l, on the y-axis.

Figure 4:
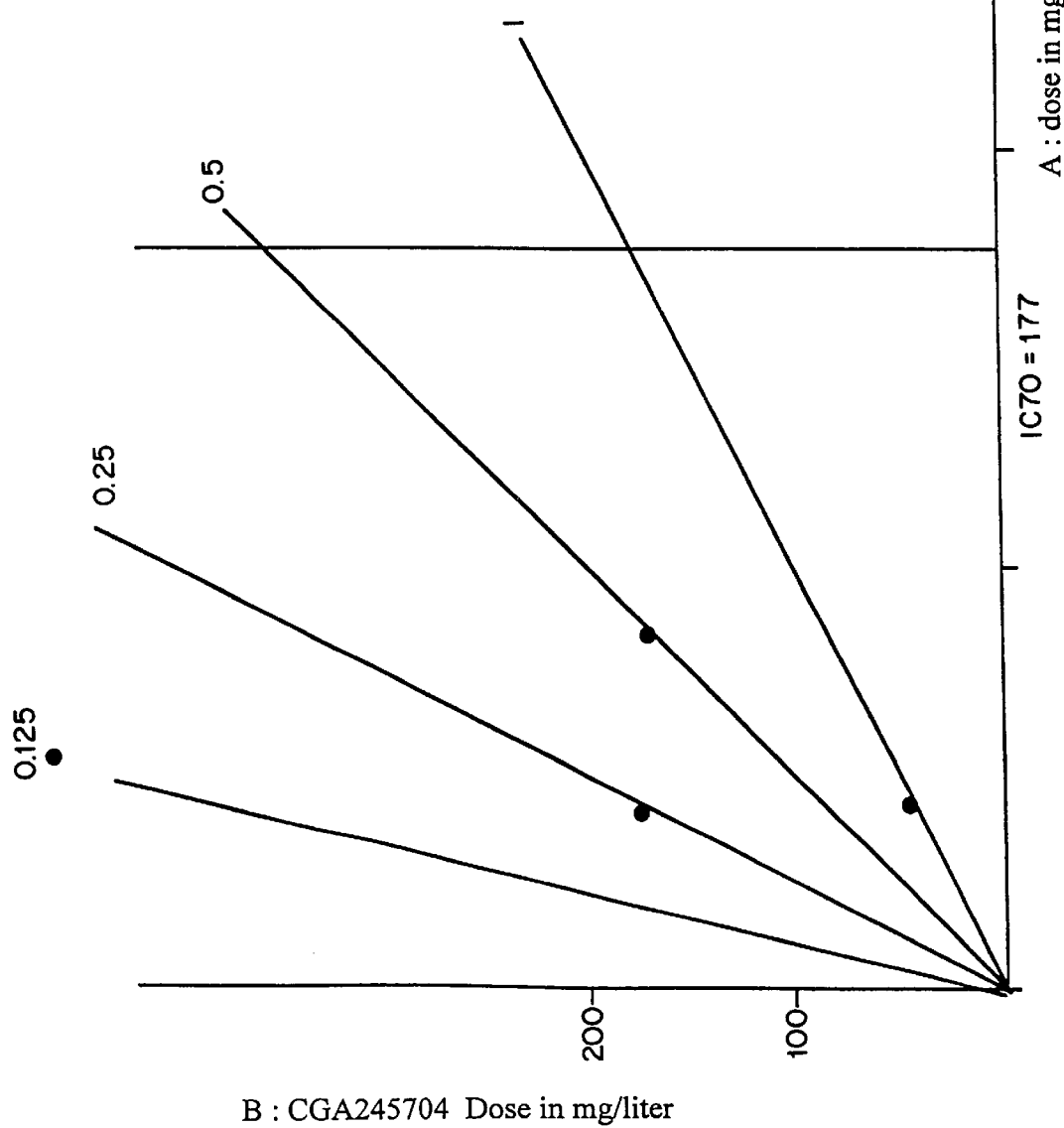
FIG. 4 shows the efficacy results obtained in Example 7 using various ratios of compound (I) and compound (IIB) (CGA245704).

The diagram of FIG. 4 is obtained, in which it appears that, when it is applied alone, CGA 245704 has no efficacy under the test conditions. It appears, however, that the addition of CGA 245704 makes it possible, entirely unexpectedly, to lower the dose of compound (I) needed to destroy 70% of the parasite to below 177 mg/l, which corresponds to the dose of compound (I) alone which needs to be applied in order to obtain the same efficacy.

The arrangement of the points obtained thus indicates a unilateral effect, termed according to the Tammes method mentioned above as a "one-sided effect". This arrangement corresponds to a type-II isobole according to the said method (page 74 of the corresponding bibliographic reference already mentioned) and is characteristic of synergism.

EXAMPLE 8

In Vivo Greenhouse Test of a Composition Comprising Compound (I) and Compound (IIC) (Cyprodinil) Against Grey Rot of Grapevine (*Botrytis cinerea*):

A 70% dispersible granule of compound (I) and a 75% dispersible granule of cyprodinil are used.

Dilute suspensions corresponding to a spraying volume of 1000 l of spraying liquid per ha are prepared from these compositions by dilution with water.

These 2 liquids are mixed together so as to obtain a compound (I)/cyprodinil ratio equal to 0.2.

Grapevine plants (Chardonnay variety) are cultivated in pots. When these plants are 2 months old, they are treated by spraying with a liquid comprising one of the compounds (I) and (IIC), either individually or as a mixture in the ratio indicated above.

After 24 hours, leaves are cut off the treated plants, placed on moistened filter paper in a Petri dish and are contaminated by applying 10 drops of an aqueous suspension of spores (containing 150,000 sp/cm$^3$) of *Botrytis cinerea*.

After this contamination, the treated and contaminated grapevine leaves are placed for 6 days at about 20° C. in an atmosphere of saturated humidity.

The results are then observed by comparison with the untreated control plants which are also contaminated.

For this, the number of drops of *Botrytis cinerea* suspension from which a grey mark, corresponding to attack by the phytopathogenic fungus, developed is counted for a grapevine leaf. This number is divided by the number of drops applied (equal to 10) and the degree of attack (expressed in %) is thus obtained.

The efficacy of the treatment (expressed in %) is calculated according to the so-called Abbott formula.

The efficacy results obtained are reported in the form of points, corresponding to 90% destruction of the parasite, and are placed in a Tammes diagram which includes the doses of cyprodinil expressed in mg/l on the x-axis and the doses of compound (I), also in mg/l, on the y-axis.

Figure 5:
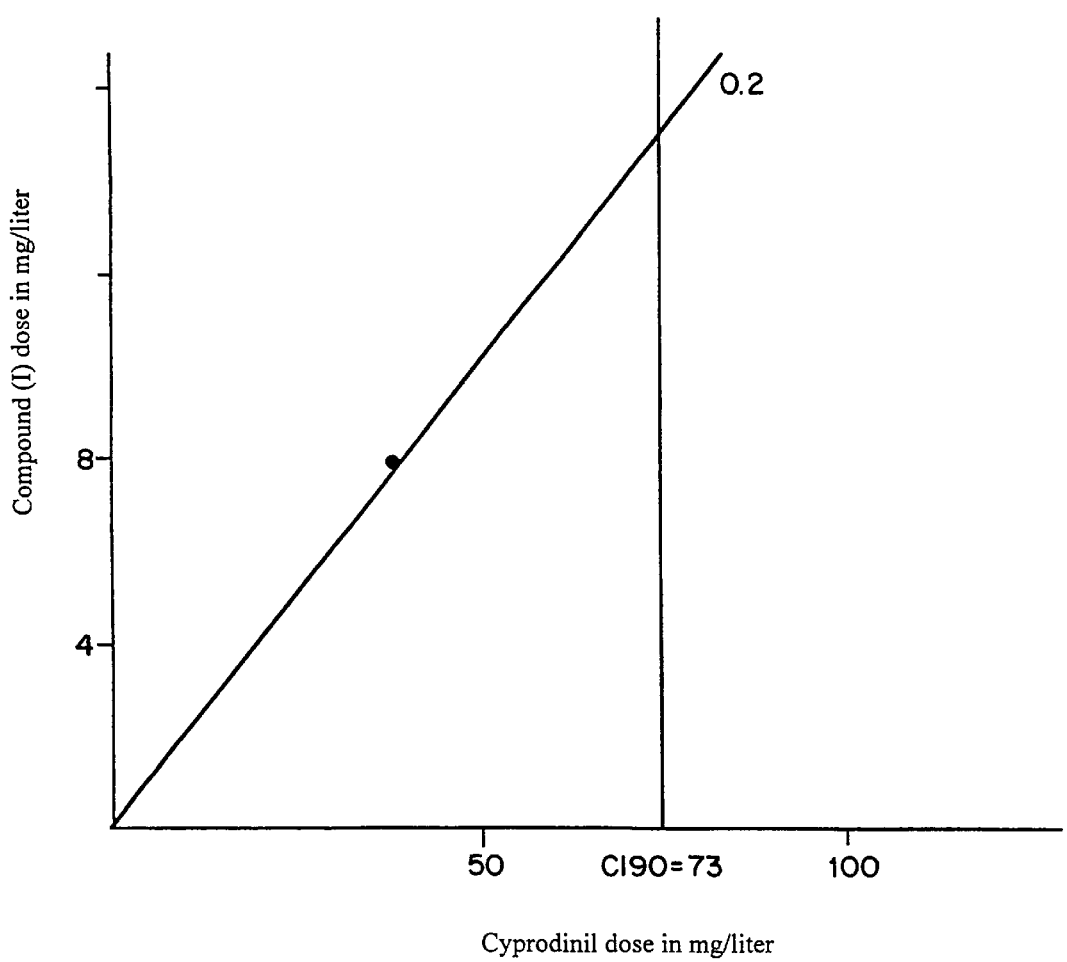
FIG. 5 shows the efficacy results obtained in Example 8 using various ratios of compound (I) and compound (IIC) (cyprodinil).

The diagram of FIG. 5 is obtained, in which it appears that, when it is applied alone, compound (I) has no efficacy under the test conditions. It appears, however, that the addition of cyprodinil makes it possible, entirely unexpectedly, to lower the dose of compound (I) needed to destroy 90% of the parasite to below 73 mg/l, which corresponds to the dose of cyprodinil alone which needs to be applied in order to obtain this same percentage of destruction.

The arrangement of the points obtained thus indicates a unilateral effect, termed according to the Tammes method mentioned above as a "one-sided effect". This arrangement corresponds to a type-II isobole according to the said method (page 74 of the corresponding bibliographic reference already mentioned) and is characteristic of synergism.

EXAMPLE 9

In Vivo Greenhouse Test of a Composition Comprising Compound (I) and Compound (IIC) (Cyprodinil) Against Alternaria Rot in Radish (*Alternaria brassicae*):

A 70% dispersible granule of compound (I) and a 75% dispersible granule of cyprodinil are used.

Dilute suspensions corresponding to a spraying volume of 1000 l of spraying liquid per ha are prepared from these compositions by dilution with water.

These 2 liquids are mixed together so as to obtain a compound (I)/cyprodinil ratio equal to 0.2–0.5–1.

Radish plantules (Pernot variety) are cultivated in pots. When these plantules have reached the 2-leaf cotyledon stage, they are treated by spraying with a liquid comprising compounds (I) and (IIC), either individually or as a mixture in the ratios indicated above.

24 hours after treatment, contamination is carried out by spraying with an aqueous suspension of spores (containing 40,000 sp/cm$^3$) of *Alternaria brassicae*.

After this contamination, the treated and contaminated plantules are placed for 10 days at about 20° C. in an atmosphere of saturated humidity.

The results are then observed, by comparison with untreated control plantules which are also contaminated.

For this, the percentage of attack of the cotyledon leaves by the fungus is assessed visually, the said attack being recognizable by brown necrosis marks. From the degree of attack thus obtained (expressed in %), the efficacy is calculated according to the Abbott formula with reference to the degree of attack of the control.

The efficacy results obtained are reported in the form of points, corresponding to 70% destruction of the parasite, and are placed in a Tammes diagram which includes the doses of compound (I) expressed in mg/l on the x-axis and the doses of cyprodinil, also expressed in mg/l, on the y-axis.

Figure 6:
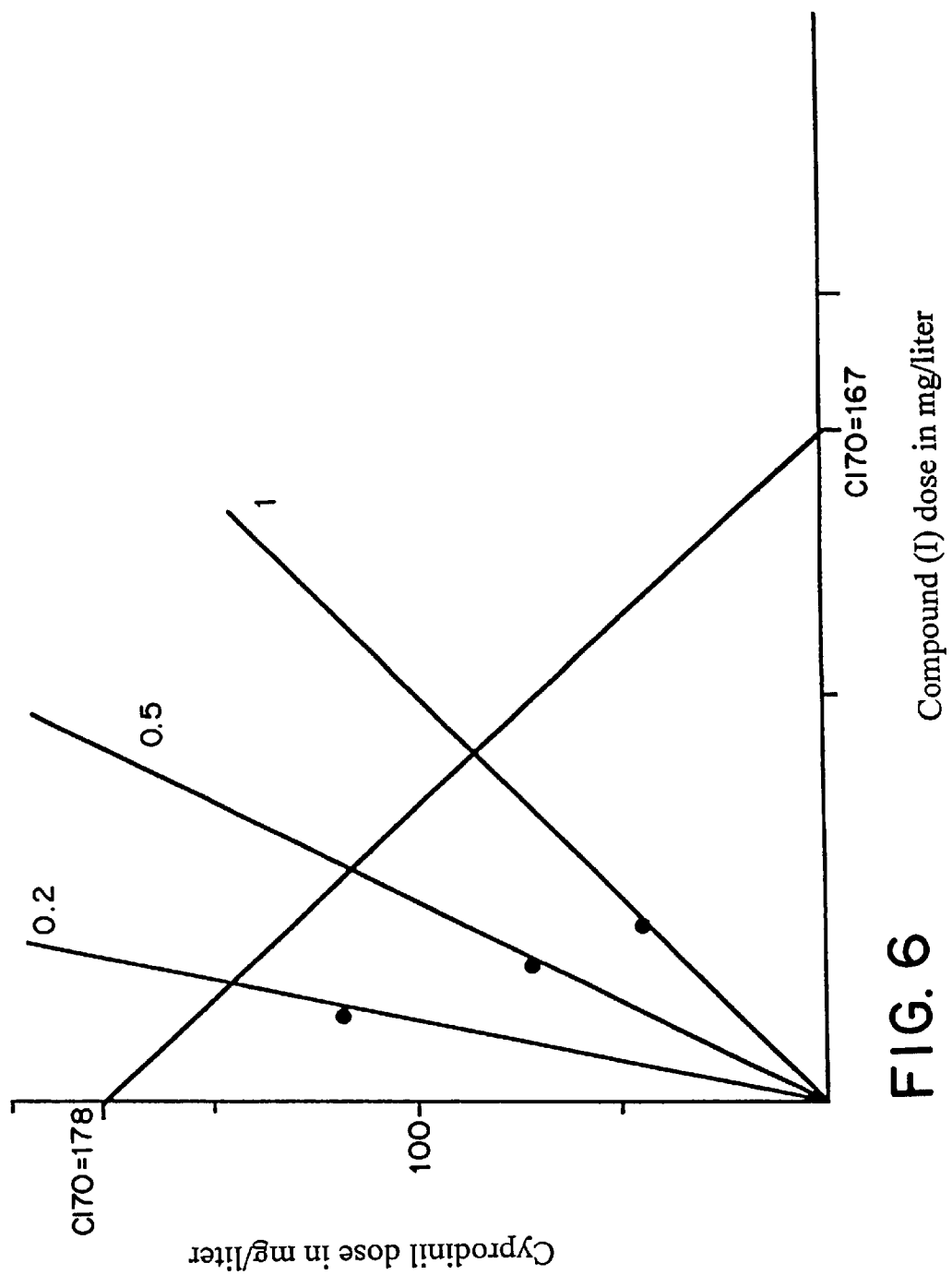
FIG. 6 shows the efficacy results obtained in Example 9 using various ratios of compound (I) and compound (IIC) (cyprodinil).

The diagram of FIG. 6 is obtained, in which it appears that the addition of a dose of compound (I) of less than 167 mg/l (which corresponds to the dose of compound (I) alone which needs to be applied in order to obtain 70% destruction of the parasite) makes it possible, entirely unexpectedly, to lower the dose of cyprodinil needed to destroy 70% of the parasite to below 178 mg/l (this value corresponding to the dose of cyprodinil alone which needs to be applied in order to obtain this same percentage of destruction).

The arrangement of the points obtained thus indicates a bilateral effect, termed according to the Tammes method mentioned above as a "two-sided effect". This arrangement corresponds to a type-III isobole according to the said method (page 75 of the corresponding bibliographic reference already mentioned) and is characteristic of synergism.

EXAMPLE 10

In Vivo Greenhouse Test of a Composition Comprising Compound (I) and Compound (IIF) (Spiroxamine) Against Powdery Mildew of Grapevine (*Uncinula necator*):

A suspension of 60 mg comprising compound (I) in a liquid mixture consisting of 0.3 ml of a surfactant (oleate of polyoxyethylenated derivative of sorbitan) diluted to 10% in water and 60 ml of water is prepared.

An emulsifiable concentrate containing 500 g/l of spiroxamine is used.

Dilute suspensions corresponding to a spraying volume of 250 l of spraying liquid per ha are prepared from these compositions by dilution with water.

These 2 liquids are mixed together so as to obtain a compound (I)/spiroxamine ratio equal to 0.33:1:3.

Grapevine plants (Chardonnay variety) are cultivated in pots. When these plants are 2 months old, they are treated by spraying with a liquid comprising one of the compounds (I) and (IIF), either individually or as a mixture in one of the ratios indicated above.

After 24 hours, the grapevine leaves are contaminated by dusting them with powdery mildew spores (*Uncinula necator*) obtained from naturally contaminated leaves.

After this contamination, the treated and contaminated grapevine plants are placed for 15 days at 20° C. at a relative humidity of about 70%.

The results are then observed by comparison with the untreated control plants which are also contaminated.

For this, the area of white marks corresponding to growth of the fungus is estimated for all of the leaves of a plant, relative to an untreated contaminated plant. A level of contamination is thus obtained.

The efficacy of the treatment (expressed in %) is calculated according to the so-called Abbott formula.

The efficacy results obtained are reported in the form of points, corresponding to 70% destruction of the parasite, and are placed in a Tammes diagram which includes the doses of spiroxamine expressed in g/ha on the x-axis and the doses of compound (I), also in g/ha, on the y-axis.

Figure 7:
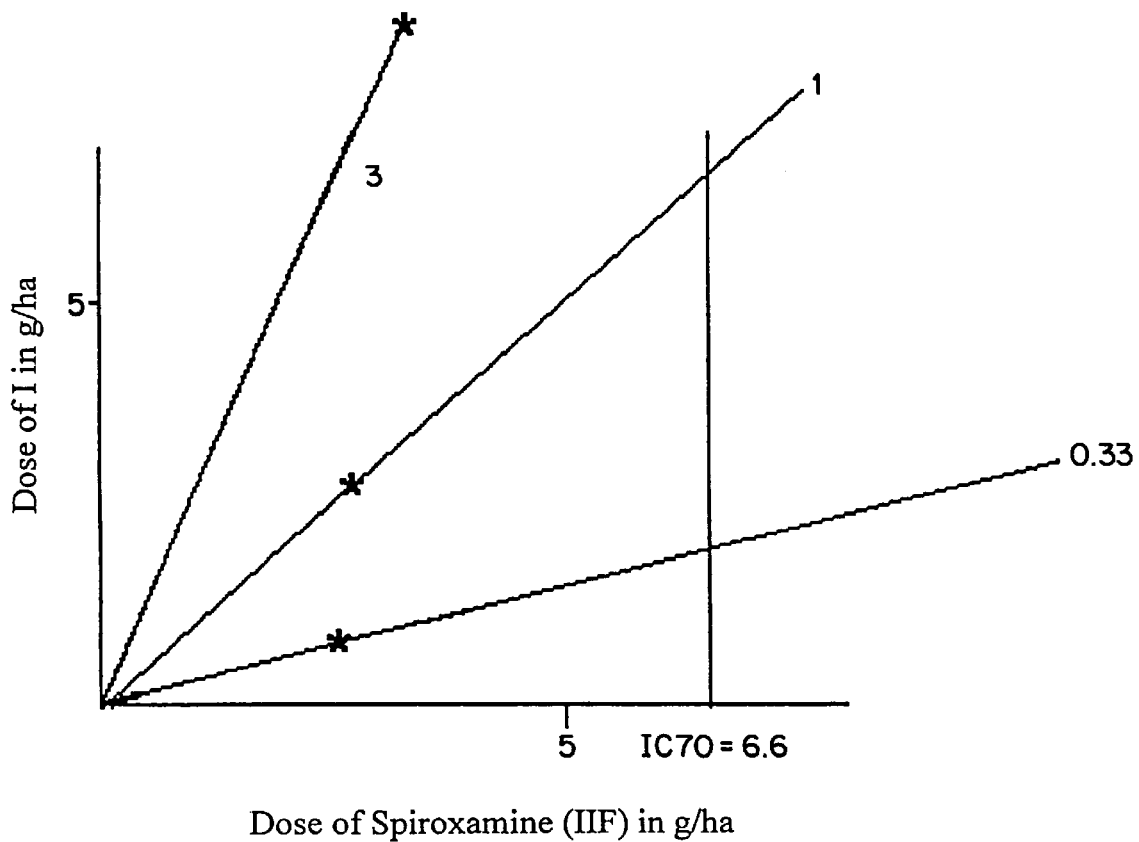
FIG. 7 shows the efficacy results obtained in Example 10 using various ratios of compound (I) and compound (IIF) (spiroxamine).

The diagram of FIG. 7 is obtained, in which it appears that, when it is applied alone, compound (I) has no efficacy under the test conditions. It appears, however, that the addition of compound (I) makes it possible, entirely unexpectedly, to lower the dose of spiroxamine needed to destroy 70% of the parasite to below 6.6 g/ha, which corresponds to the dose of spiroxamine alone which needs to be applied in order to obtain this same percentage of destruction.

The arrangement of the points obtained thus indicates a unilateral effect, termed according to the Tammes method mentioned above as a "one-sided effect". This arrangement corresponds to a type-II isobole according to the said method (page 74 of the corresponding bibliographic reference already mentioned) and is characteristic of synergism.

EXAMPLE 11

In Vivo Greenhouse Test of a Composition Comprising Compound (I) and Compound (IIF) (Spiroxamine) Against Powdery Mildew of Grapevine (*Uncinula necator*):

Example 10 is repeated, setting the compound (I)/spiroxamine ratio to 0.11:0.33 and 1 and observing the results 22 days after contamination.

Figure 8:
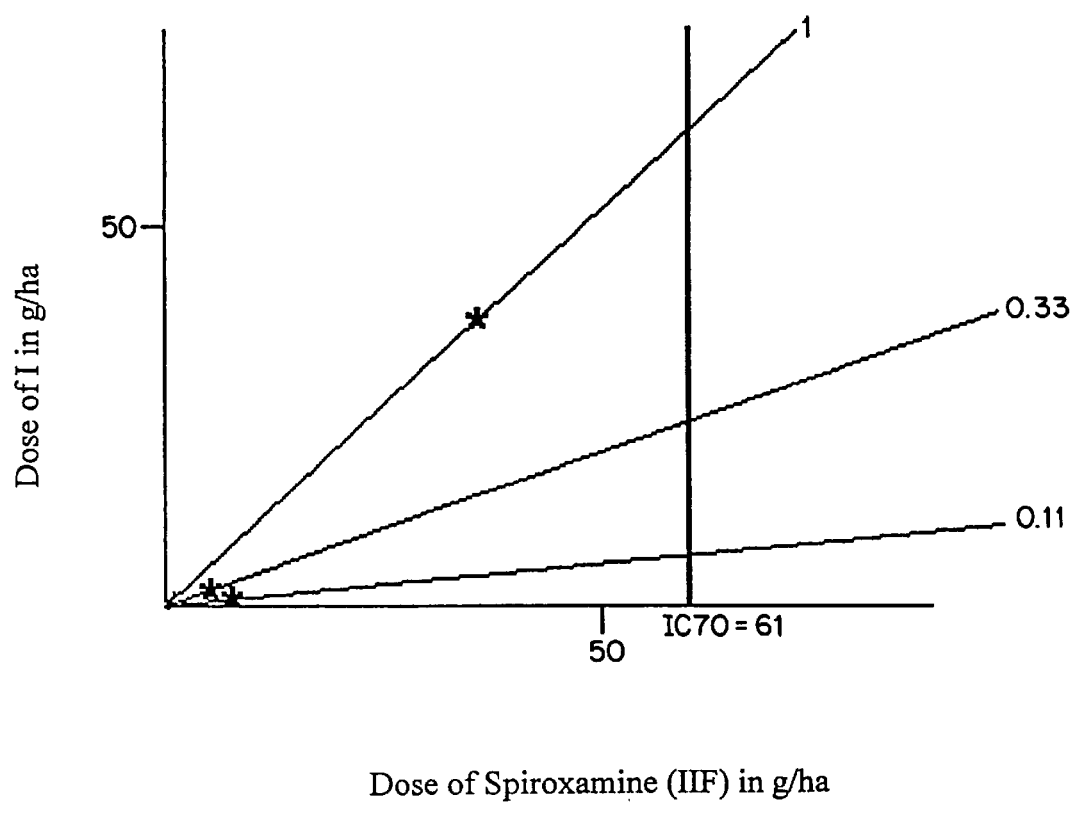
FIG. 8 shows the efficacy results obtained in Example 11 using various ratios of compound (I) and compound (IIF) (spiroxamine).

The diagram of FIG. 8 is obtained, in which it appears that, when it is applied alone, compound (I) has no efficacy under the test conditions. It appears, however, that the addition of compound (I) makes it possible, entirely unexpectedly, to lower the dose of spiroxamine needed to destroy 70% of the parasite to below 61 g/ha, which corresponds to the dose of spiroxamine alone which needs to be applied in order to obtain this same percentage of destruction.

The arrangement of the points obtained thus indicates a unilateral effect, termed according to the Tammes method mentioned above as a "one-sided effect". This arrangement corresponds to a type-II isobole according to the said method (page 74 of the corresponding bibliographic reference already mentioned) and is characteristic of synergism.

EXAMPLE 12

In Vivo Greenhouse Test of a Ternary Composition Comprising Compounds (I), IIG (Fencaramide) and IIG' (Fosetyl-Al) Against Downy Mildew of Grapevine (*Plasmopara viticola*):

A 70% dispersible granule of compound I, a 50% dispersible granule of fencaramide and an 80% dispersible granule of Fosetyl-Al are used.

Dilute suspensions corresponding to a spraying volume of 1000 l/ha are prepared from these compositions by dilution with water. The dilute suspensions of fencaramide and of Fosetyl-Al are mixed together so as to obtain a stock suspension comprising these 2 active materials in a fixed Fencaramide/Fosetyl-Al ratio equal to 0.1.

The dilute suspension of compound (I) and this stock suspension are mixed together so as to obtain a mixture of the 3 active materials in the compound (I)/Fencaramide+Fosetyl-Al ratio equal to 1/(1+10) (i.e. 0.09) and 2/(1+10) (i.e. 0.18).

Grapevine (Chardonnay variety) cuttings are cultivated in pots. When these plants are 2 months old (8- to 10-leaf growth stage), they are treated by spraying with a liquid comprising either compound (I) alone or the mixture Fencaramide+Fosetyl-Al, or the mixture of the 3 active materials. The spraying volume of 1000 l/ha allows coverage of the lower and upper faces of the leaves.

The treated plants were contaminated beforehand (24 hours before the fungicidal treatment) by spraying with an aqueous suspension of *Plasmopara viticola* spores (100,000 sp/cm$^3$). After contamination, the plants are left at room temperature for 1 hour at 70% relative humidity, then for 24 hours at 90 to 100% relative humidity, before receiving the fungicidal treatment.

After the fungicidal treatment, the plants are maintained for 1 hour in an atmosphere at 70% relative humidity and are then left for 7 days at 90 to 100% relative humidity.

The results are then observed by comparison with the untreated control plants which are also contaminated. For this, the contaminated fraction (estimated in %) of the lower surface of the leaves is determined by visual evaluation.

The efficacy results obtained are reported in the form of points, corresponding to 70% destruction of the parasite, and are placed in a Tammes diagram which includes the doses of compound (I) expressed in mg/l on the x-axis and the doses of the fencaramide+fosetyl-Al mixture (in a 1/10 ratio), expressed in the form of a single dose of fencaramide in the mixture, in mg/l, on the y-axis.

The diagram of FIG. 9 is obtained, in which it appears that the addition of a dose of compound (I) of less than 36 mg/l (which corresponds to the dose of compound (I) alone which needs to be applied in order to obtain 70% destruction of the parasite) makes it possible, entirely unexpectedly, to lower the dose of the fencaramide/fosetyl-Al mixture (in the ratio 1/10) to well below 34 mg/l (this value corresponding to the equivalent dose of fencaramide in the said mixture which needs to be applied in order to obtain this same percentage of destruction).

The arrangement of the points obtained thus indicates a bilateral effect, termed according to the Tammes method mentioned above as a "two-sided effect". This arrangement corresponds to a type-III isobole according to the said method (page 75 of the corresponding bibliographic reference already mentioned) and is characteristic of synergism.

What is claimed is:

1. Fungicidal compositions comprising an active material mixture, wherein said active material mixture consists essentially of synergistic fungicidally effective amounts of:

(a) compound (I) of formula:

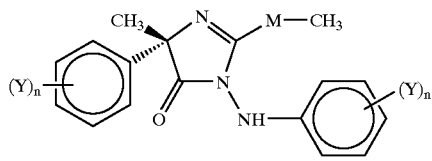

in which:
   M represents a sulphur atom;
   n is an integer equal to 0 or 1;
   Y is a fluorine or chlorine atom or a methyl radical;
(b) a compound (II) which is iprovalicarb;
   wherein the compound (I)/compound (II) ratio is from 0.25 to 5, and, optionally,
(c) a salt of a monoalkyl phosphite and a mono-, di-, or trivalent metal cation; or, optionally;
(d) a phosphorus acid or its alkali- metal or alkaline-earth metal salts.

2. Fungicidal compositions according to claim 1, wherein the compound (I) is (4S)-4-methyl-2-methylthio-4-phenyl-1-phenylamino-2-imidazolin-5-one.

3. Fungicidal compositions according to claim 1, wherein the compound (I)/compound (II) ratio is from 0.5 to 4.

4. Fungicidal compositions according to claim 1, wherein the salt of a monoalkyl phosphite and a mono-, di- or trivalent metal cation is present, and the molar ratio of iprovalicarb to the salt is from 0.018 to 1.8.

5. Fungicidal compositions according to claim 1, wherein the salt of a monoalkyl phosphite and a mono-, di- or trivalent metal cation is present, and the molar ratio of iprovalicarb to the salt is from 0.037 to 0.37.

6. Fungicidal compositions according to claim 1, wherein the phosphorous acid or its alkali-metal or alkaline-earth metal salts is present, and the molar ratio of iprovalicarb to the phosphorous acid or salt thereof is from 0.018 to 1.8.

7. Fungicidal compositions according to claim 1, wherein the phosphorous acid or its alkali-metal or alkaline-earth metal salts is present, and the molar ratio of iprovalicarb to the phosphorous acid or salt thereof is from 0.037 to 0.37.

8. Fungicidal compositions according to claim 4, wherein the salt is fosetyl-Al.

9. Fungicidal compositions according to claim 5, wherein the salt is fosetyl-Al.

10. Fungicidal compositions comprising an active material mixture, wherein said active material mixture consists essentially of synergistic fungicidally effective amounts of:
   (a) a compound (I) of formula:

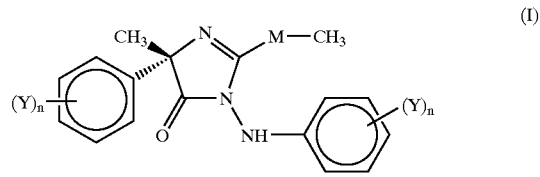

in which:
      M represents a sulphur atom;
      n is an integer equal to 0 or 1;
      Y is a fluorine or chlorine atom or a methyl radical;
   (b) a compound (IIG) which is iprovalicarb; and
   (c) a compound (IIG') which is fosetyl-Al;
   wherein the compound (I)/compound (IIG) ratio is from 0.25 to 5 and the compound (IIG)/compound (IIG') ratio is from 0.018 to 1.8.

11. Fungicidal compositions according to claim 10, wherein the compound (IIG)/compound (IIG') ratio is from 0.018 to 1.8.

* * * * *